US010798954B2

(12) United States Patent
Vercauteren

(10) Patent No.: US 10,798,954 B2
(45) Date of Patent: Oct. 13, 2020

(54) REMOVAL OF PHYTATE

(71) Applicant: CARGILL, INCORPORATED, Wayzata, MN (US)

(72) Inventor: Ronny Leontina Marcel Vercauteren, Beveren (BE)

(73) Assignee: BOORTMALT NV, Antwerp (BE)

( * ) Notice: Subject to any disclaimer, the term of this patent is extended or adjusted under 35 U.S.C. 154(b) by 726 days.

(21) Appl. No.: 15/317,491

(22) PCT Filed: Jun. 12, 2015

(86) PCT No.: PCT/US2015/035502
§ 371 (c)(1),
(2) Date: Dec. 9, 2016

(87) PCT Pub. No.: WO2015/191966
PCT Pub. Date: Dec. 17, 2015

(65) Prior Publication Data
US 2017/0099861 A1    Apr. 13, 2017

(30) Foreign Application Priority Data
Jun. 12, 2014 (EP) ..................................... 14172185

(51) Int. Cl.
| | |
|---|---|
| *A23L 5/20* | (2016.01) |
| *A23L 7/10* | (2016.01) |
| *A23L 11/00* | (2016.01) |
| *A23L 11/30* | (2016.01) |
| *A23K 10/30* | (2016.01) |
| *A61K 8/97* | (2017.01) |
| *A61Q 19/00* | (2006.01) |
| *A61K 8/55* | (2006.01) |
| *A23L 33/105* | (2016.01) |

(52) U.S. Cl.
CPC ................ *A23L 5/20* (2016.08); *A23K 10/30* (2016.05); *A23L 7/197* (2016.08); *A23L 7/198* (2016.08); *A23L 11/01* (2016.08); *A23L 11/05* (2016.08); *A23L 11/30* (2016.08); *A23L 33/105* (2016.08); *A61K 8/55* (2013.01); *A61K 8/97* (2013.01); *A61Q 19/00* (2013.01); *A23V 2002/00* (2013.01); *A61K 2800/10* (2013.01); *A61K 2800/805* (2013.01)

(58) Field of Classification Search
CPC ......... A23K 10/30; A23L 11/01; A23L 11/05; A23L 11/30; A23L 33/105; A23L 5/20; A23L 7/197; A23L 7/198; A23V 2002/00; A61K 2800/10; A61K 2800/805; A61K 8/55; A61K 8/97; A61Q 19/00
See application file for complete search history.

(56) References Cited

U.S. PATENT DOCUMENTS 6,139,892 A * 10/2000 Fredlund .................. A23B 9/00
426/458

FOREIGN PATENT DOCUMENTS

| WO | 199811788 A1 | 3/1998 | |
|---|---|---|---|
| WO | WO-9811788 A1 * | 3/1998 | ............... A23B 9/00 |
| WO | 200072700 A1 | 12/2000 | |
| WO | 2003080248 A1 | 10/2003 | |
| WO | 2005094606 A2 | 10/2005 | |
| WO | 2010108277 A1 | 9/2010 | |
| WO | 2012143626 A1 | 10/2012 | |

OTHER PUBLICATIONS

Liang J; Han B-Z; Nout, MJ; HAmer RJ "Effects of soaking, germination and fermentation on phytic acid, total and in vitro soluble zinc in brown rice" Food Chemistry, 2008, 110(4), pp. 821-828; doi:10.1016/j.foodchem.2008.02.064. (Year: 2008).*
International Search Report dated Sep. 18, 2015 for International Application No. PCT/US2015/035502 (5 pages).

* cited by examiner

*Primary Examiner* — Aaron J Kosar
(74) *Attorney, Agent, or Firm* — Kagan Binder, PLLC

(57) ABSTRACT

The present invention relates to a steeping process for reducing the phytate in kernels of cereals and/or pulses using endogenous phytase. The kernels are steeped in water whilst avoiding germination and then dried. The steeped kernels and/or flour made therefrom are used in food, feed, pet-food, and/or cosmetics.

9 Claims, No Drawings

REMOVAL OF PHYTATE

CROSS-REFERENCE TO RELATED APPLICATIONS

This application is a national pulse application of PCT/US2015/035502, filed 12 Jun. 2015, which claims the benefit of European Application Serial No. 14172185.2 filed 12 Jun. 2014, the disclosures of which are incorporated herein by reference in their entirety.

FIELD OF THE INVENTION

The present invention relates to the reduction of phytate in cereals and/or pulses.

BACKGROUND OF THE INVENTION

Essentially all food and feed substances originating from plants contain phytate and phytic acid (is inositol hexakis-phosphate) as a storage phosphorous source. About 75-78% of the phosphorous in cereals is bound as phytic acid.

Phytate is not digestible by humans or nonruminant animals, so it is not a source of either inositol or phosphate if eaten directly.

Furthermore, phytic acid chelates minerals such as calcium, zinc, magnesium, and iron, thereby decreasing the bio-availability of nutritionally important minerals and is as such considered as an anti-nutritional factor.

The bio-availability of phytate phosphorous can be increased by supplementation of the diet with the enzyme phythase. Phythases are enzymes which catalyze the conversion of phytate to inositol and inorganic phosphorous. Phythases can be obtained from e.g. *Bacillus, Pseudomonas, Saccharomyces* and *Aspergillus*.

Simply cooking the food will reduce the phytic acid to some degree. More effective methods are soaking in an acid medium, lactic acid fermentation, and sprouting.

The use of sprouted grains will reduce the quantity of phytic acids in feed, with no significant reduction of nutritional value. Germination results in a marked fall in phytate-phosphorous. However during the germination, sprouting occurs and the kernels are broken.

It would be desirable to have a simple, mild but effective process for the removal of phytate while maintaining the kernels intact.

The current invention provides such a process.

SUMMARY OF THE INVENTION

The current invention relates to a process for treating kernels of cereals and/or pulses, comprising the following steps:
a) Steeping of the kernels while germination of the kernels is avoided and the kernels are un-milled and the kernels are, without water immersions, soaked in a volume of water that is from 0.8 to 10 times the weight of the kernels, the steeping is performed at a temperature of from 50 to 70° C. during a period of from 8 to 72 hours and during the steeping pH is from 3.5 to 6.5,
b) Optionally draining excess of water,
c) Drying the steeped kernels at a temperature of from 50 to 120° C.

Furthermore it relates to the use of endogenous phytase in a steeping process to reduce the phytate in kernels of cereals and/or pulses and the use of steeped kernels in food, feed, pet-food, and/or cosmetics.

DETAILED DESCRIPTION

The current invention relates to a process for treating kernels of cereals and/or pulses, comprising the following steps:
a) Steeping of the kernels while germination of the kernels is avoided and the kernels are un-milled and the kernels are, without water immersions, soaked in a volume of water that is from 0.8 to 10 times the weight of the kernels, the steeping is performed at a temperature of from 50 to 70° C. during a period of from 8 to 72 hours and during the steeping pH is from 3.5 to 6.5,
b) Optionally draining excess of water,
c) Drying the steeped kernels at a temperature of from 50 to 120° C.

Steeping corresponds to the first step in the well-known malting process. As it is known, the malting process consists primarily of three stages: steeping, germination and kilning. In general, the steeping refers to the immersion of the grain kernels in water to increase the moisture content of the kernels. The germination refers to a period of controlled growth and modification of the kernels, and this modification of the kernels encompass cell wall degradation in the starchy endosperm, creation of soluble proteins and free amino nitrogen, and synthesis of desirable enzymes. Kilning refers to the controlled drying of the germinated kernels. As it can be seen, it is well-known to have enzymes freed up during the germination step, but this result also in sprouting of the kernels. It has surprisingly been found that a steeping process without a subsequent germination, is sufficient for reducing the phytate content of the kernels of cereals and/or pulses. The steeping process of the current invention allows reducing the content of phytate of the kernels while the kernels remain intact. In fact, the content of phytate is reduced for more than 50 weight %, more than 60 weight %, more than 70 weight %, even more than 80 weight %, up to 95 weight %. While in a "classical" steeping process of barley, the barley kernels are immersed in water and may involve several immersions to limit the bacterial spoilage, the current process is qualified such that there are no water immersions of the steeping and the volume of steeping water is limited in order to avoid leaching of valuable micronutrients and the kernels are soaked in a volume of water that is from 0.8 to 10 times the weight of the kernels. The process of the current invention applies a minimum amount of water, thus allowing a maximum water absorption by the kernel and there is almost no draining needed.

The process of the current invention involves one steeping step wherein the kernels are soaked in a volume of water that is from 0.8 to 10 times the weight of the kernels.

The steeping step or where applicable the step of drainage is immediately followed by a drying step.

Furthermore, the process of the current invention uses un-milled kernels of cereals and/or pulses.

The process of the present invention is characterized in that the cereals and/or pulses are selected from the group consisting of rice, wheat, oat, soy, corn, chick pea, barley, lentils, and mixtures of two or more thereof. Preferably wheat, corn, oat or rice is used, more preferably rice is used in the process of the present invention.

The steeping is performed at a temperature of from 50 to 70° C. during a period of from 8 to 72 hours. The temperature of the current process allows suppressing the germination and/or sprouting of the kernels. Furthermore, the temperature of the current process allows shortening the reaction time. During the time of the current process the enzyme activity is increased and the enzyme produced in the kernel (i.e. the endogenous phythase) allows reduction of phytate of at least 50% of the total amount of phytate present in the original kernels of cereals and/or pulses. Surprisingly it was found that the endogenous phytase present in the intact kernel is able to significantly reduce the phytate in the kernels. The content of phytate is reduced for more than 50 weight %, more than 60 weight %, more than 70 weight %, even more than 80 weight %, up to 95 weight %.

The process of the present invention is further characterized in that during the steeping, pH is from 3.5 to 6.5, which corresponds to the optimum pH for the phythase.

The steeping of the current invention is characterized in that the kernels are soaked in a volume of water that is from 0.8 to 10 times the weight of the kernels. The amount of water is such that it is sufficient to wet or soak the kernels. The low amounts of water allow that the swollen kernels can be dried without having to drain an excess of water. In a process where there is no drainage of an excess of water, all micronutrients are maintained in the swollen kernels. While in a so-called "classical" steeping process the water is refreshed several times, to avoid bacterial spoilage, the process of the current invention uses low amounts of water, such as from 0.8 to 10 times the weight of the kernel and consequently, the subsequent drying step is requiring significantly less energy and the micronutrients are maintained with the kernels.

Furthermore, the process of the current invention is characterized in that the steeping step is performed in an open system and the kernels are soaked in a volume of water that is from 4 to 10 times the weight of the kernels, optionally followed by replenishing with water to compensate for the evaporated water. The total amount of water including the optional replenishment is not more than 10 times the weight of the kernels. In the open system the kernels are aerated and this aeration allows for a limited evaporation of the water. Replenishing of water is sometimes needed to compensate for this loss of water due to aeration. For the open system, preferably the temperature is from 50 to 55° C., at a pH of 4 to 6 for a period of time of 24 hours to 48 hours. The process of the current invention in an open system still allows for obtaining kernels with reduced phytate of at least 40% of the total amount of phytate present in the original kernels of cereals and/or pulses and the kernels are still intact.

Alternatively, the process of the present invention is characterized in that the steeping step is performed in a closed system and the kernels are soaked in a volume of water that is from 0.8 to 4 times the weight of the kernels, preferably from 1 to 3 times the weight of the kernels. The closest system provides in addition the advantage that there is no loss of water through evaporation at the surface. The lack of evaporation further allows a reduction of the amount of water that is needed in the process. A more simplified drying (less energy requirements) can be foreseen. The kernels are softened while the structural integrity is maintained, which makes it more easy and efficient for the subsequent process steps such as the drying step. Preferably in the closest system, the temperature is from 50° C. to 70° C., at a pH of 3.5 to 6.5 and during a period of time of 8 to 72 hours.

The process of the current invention allows the reduction of at least 50% if the initial amount of phytate (phytate+ phytic acid), preferably at least 60%, more preferably at least 80%. While the process of the current invention does not involve a germination step, it provides as such a process where the risk of chitting and rootlet formation is minimal.

The drying of the steeped kernels of cereals and/or pulses can be performed in any suitable drying equipment at a temperature of from 50 to 120° C. Eventually the drying can be done in the kilning facility of the malting process and may involve hot air. During the drying of the steeped kernels the temperature is usually raised from 50-65° C. to 80-120° C., eventually with reduced pressure, or from 50-65° C. to 80-85° C. and the moisture content of the steeped kernels is reduced from 40-45% to 4-5% in a time of about 24 hours.

The drying step may have an effect on the final product colour, and further flavor development of the steeped kernels. The drying step may form flavor and body-building melanoidins from the amino acids and malt sugars in the malt.

The process of the current invention provides intact kernels, swollen and softened and with a cleaner taste than the starting material, e.g. less of the so called "cereal taste".

The thus obtained dried steeped kernels of cereals and/or pulses can be directly applied in any food material, feed, pet-food, and/or cosmetics.

The advantages of the steeped kernels is the reduced amount of phytate, consequently the increased amount of minerals, and due to the swollen state, the boiling or cooking time of these steeped kernels is significantly reduced.

The process of the current invention may further have a step wherein the steeped kernels are reduced in size and provide flour with a reduced content of phytate.

The kernels of the current invention are softened and during the application in cooking processes, the cooking time can be reduced.

Furthermore it has been shown that the steeping process of the current invention has an effect on the gelatinization profile/onset.

The current invention relates to the use of a steeping process for the reduction of phytate in kernels of cereals and/or pulses, wherein endogenous phythase of kernels is reducing the phytate.

The current invention further relates to the use of the steeped kernels and/or flour of steeped kernels obtainable by the process of the current invention in food, feed, pet-food, and/or cosmetics.

The invention will hereunder be illustrated in following examples.

EXAMPLES

Methodology

Measurement of Phytic Acid:
Measured with Megazyme's Kit K-PHYT

Example 1—Open System—Temerature—No pH Adjustment

In a first set of experiments, the effect of temperature (30, 40, 50° C.) on phytic acid reduction was studied. For each experiment, at a certain temperature and soaking time: 1 kg of rice was soaked in 10 l water. Except for the experiments done at 50° C.: 4 kg rice in 25 l water of which 1 kg is removed after the different soaking times: 6, 12, 24 and 48 hours. The 6 hours sample was not analyzed. A water change was done every 6 hours, except after 18 and after 42 hours. Drying of the rice samples was done for 24-36 hours at 80° C. Aeration was accomplished by a tube with pressurized air going to the bottom of the steep vessel.

pH 3.5 or 4.5 adjustment with 20% w/w citric acid or, pH 5.0 adjustment with 20% w/w lactic acid solution in water.

| Code | Steep | Phytic acid (% db) | Phytic acid reduction (%) |
|---|---|---|---|
| 1 | Start material | 1.28 | |
| 2 | 30° C., 12 H | 1.26 | 1.3 |
| 3 | 30° C., 24 H | 1.13 | 11.5 |
| 4 | 30° C., 48 H | 1.00 | 22.3 |
| 5 | 40° C., 12 H | 1.17 | 8.5 |
| 6 | 40° C., 24 H | 1.11 | 13.4 |
| 7 | 40° C., 48 H | 1.13 | 11.4 |
| 8 | 50° C., 12 H | 0.76 | 40.3 |
| 9 | 50° C., 24 H | 0.65 | 49.4 |
| 10 | 50° C., 48 H | 0.67 | 47.3 |

Example 2—Open System—pH Adjustment

The set-up is the same as in Example 1, except for the pH adjustment. The pH 3.5 adjustment was done with 20% w/w citric acid or, for pH 5.0 adjustment with 20% w/w lactic acid solution in water.

| Code | Temp (° C.) | Steep (H) | pH adjustment | pH steep | Phytic acid db (%) % db | % decrease |
|---|---|---|---|---|---|---|
| 11 | — | — | Untreated rice | | 1.154 | |
| 12 | 50 | 24 | Lactic 2nd water | 5.0 | 0.55 | 52.3 |
| 13 | 50 | 48 | Lactic 2nd water | | 0.315 | 72.7 |
| 14 | 50 | 24 | none | 8.5 | 0.588 | 49.0 |
| 15 | 50 | 48 | none | | 0.522 | 54.8 |
| 16 | 50 | 24 | citric acid | 3.5 | 0.336 | 70.9 |
| 17 | 50 | 48 | citric acid | | 0.118 | 89.8 |
| 18 | 50 | 24 | lactic acid | 5.0 | 0.482 | 58.2 |
| 19 | 50 | 48 | lactic acid | | 0.286 | 75.2 |
| 20 | 30 | 24 | none | 7.7-8.4 | 0.935 | 19.0 |
| 21 | 30 | 48 | none | | 0.826 | 28.4 |
| 22 | 30 | 24 | citric acid | 3.5 | 0.848 | 26.5 |
| 23 | 30 | 48 | citric acid | | 0.745 | 35.4 |
| 24 | 30 | 24 | lactic acid | 5.0 | 0.814 | 29.5 |

The best results of phytate reduction are obtained at 50° C., pH 3.5, 48H: ~90% reduction.

Example 3—Open System

No refreshment of wash water, and use of minimal amount of water so that no extensive drainage after steeping was required Less or normal aeration: a tube with pressurized air, going to the bottom of the steep vessel pH 3.5 or 4.5 adjustment, with 20% w/w citric acid or, pH 5.0 adjustment with 20% w/w lactic acid solution in water.

24, 48, 60 hr incubation time

Drying at 80° C. for 24 hr

| Code | pH (—) | T (° C.) | Time (H) | Aeration | kg rice/l water | Washing before and after soak | d.s (%) | Phytic acid (g/100 g db) | Phytic acid Reduction (%) |
|---|---|---|---|---|---|---|---|---|---|
| 26 | | Rice at start | | | | | 88.4 | 1.123 | — |
| 27 | 3.5 | 50 | 24 | less | 0.75/3 | not | 98.0 | 0.315 | 72.0 |
| 28 | 3.5 | 50 | 48 | less | 0.75/3 | not | 96.9 | 0.279 | 75.1 |
| 29 | 3.5 | 50 | 60 | less | 0.75/3 | not | 98.1 | 0.250 | 77.7 |
| 30 | 4.5 | 50 | 24 | less | 0.75/3 | not | 97.4 | 0.405 | 63.9 |
| 31 | 4.5 | 50 | 48 | less | 0.75/3 | not | 97.1 | 0.175 | 84.4 |
| 32 | 4.5 | 50 | 60 | less | 0.75/3 | not | 98.0 | 0.147 | 86.9 |
| 33 | 3.5 | 50 | 48 | normal | 0.75/(2 + 0.5) | done | 98.6 | 0.292 | 77.0 |
| 34 | 4.5 | 50 | 48 | normal | 0.75/(2 + 0.5) | done | 98.9 | 0.172 | 86.4 |
| 35 | 4.5 | 50 | 48 | normal | 0.75/(2 + 0.5) | not | 98.6 | 0.185 | 85.4 |
| 36 | 4.0 | 50 | 48 | normal | 0.75/3 | done | 98.2 | 0.101 | 90.3 |
| 37 | 5.0 | 50 | 48 | normal | 0.75/3 | done | 97.8 | 0.103 | 90.0 |
| 38 | 4.5 | 50 | 48 | normal | 0.75/3 | done | 95.8 | 0.097 | 90.6 |
| 39 | 5.5 | 50 | 48 | normal | 0.75/3 | done | 96.0 | 0.221 | 78.6 |

Explanation of Results

A reduction is aeration had only a small impact on the results. Washing the kernels before and after the steep, had no influence on the phytate reduction, as measured. Less aeration gave the onset of lactic acid fermentation. Best results were obtained for the pH 4 till 5, with a reduction in phytate of about 85-90%.

Example 4—Closed System

The cereals are twice rinsed in a 15 ml Falcon tube. Water is added to get a dry substance of 20% (w/w) brown rice. The pH adjusted to 5 with 20% citric acid and the closed tubes are placed in a Thermomixer confort for 48 hours at 60 or 65° C.

| Sample | Phytic acid db (g/100 g) | Decrease (%) |
|---|---|---|
| Rice 4R0 | 0.840 | |
| Maize | 0.726 | |
| Wheat | 0.999 | |
| rice 60° C. | 0.280 | 66.7 |
| maize 60° C. | 0.269 | 62.9 |
| Wheat 60° C. | 0.373 | 62.6 |
| rice 65° C. | 0.522 | 37.9 |
| maize 65° C. | 0.208 | 71.4 |
| Wheat 65° C. | 0.407 | 59.3 |

Heating rice, wheat or maize to 60° C. gives a significant reduction of the amount of phytate. An increase of the steeping temperature to 65° C. has a positive effect on the reduction of phytate in maize. For rice and wheat, an increase to 65° C. results in a decrease of the phytate degradation.

Example 5—Closed System

The soaking trials are now done with less water, buffered (B) or non-buffered (W). 56% or 38% of brown rice (w/w) in water adjusted to pH 5 with 5% citric acid or 0.1M NaAc/HAc buffer pH 5.

| Code | Grain | Time (H) | T (° C.) | % rice (g/100 g) | Water or Buffer | phytic acid on db (g/100 g) | phytic acid reduction (%) |
|---|---|---|---|---|---|---|---|
| 49 | Wheat | 0 | | | | 0.934 | |
| 50 | Maize | 0 | | | | 0.907 | |
| 51 | Brown Rice | 0 | | | | 0.840 | |
| 52 | Brown Rice | 24 | 60 | 56 | W | 0.345 | 58.9 |
| 53 | Brown Rice | 24 | 60 | 56 | B | 0.330 | 60.8 |
| 54 | Brown Rice | 48 | 60 | 56 | B | 0.309 | 63.2 |
| 55 | Brown Rice | 24 | 60 | 38 | W | 0.481 | 42.8 |
| 56 | Brown Rice | 48 | 60 | 38 | W | 0.287 | 65.8 |
| 57 | Wheat | 24 | 60 | 56 | W | 0.380 | 59.3 |
| 58 | Wheat | 48 | 60 | 56 | W | 0.412 | 56.0 |
| 59 | Wheat | 24 | 60 | 38 | B | 0.338 | 63.8 |
| 60 | Maize | 24 | 65 | 56 | W | 0.679 | 25.1 |
| 61 | Maize | 48 | 65 | 56 | W | 0.584 | 35.6 |
| 62 | Maize | 24 | 65 | 38 | W | 0.467 | 48.5 |
| 63 | Maize | 48 | 65 | 38 | W | 0.391 | 56.9 |

Incubating the wheat at 56% w/w in water has not the best impact on the reduction of the phytic acid: the phytic acid content after 48 soaking at 60° C. was reduced with 53%. Using the brown rice at 38% (w/w) in steep water, gives a reduction of 66% after 48 h incubation.
Using a buffer system to steep the brown rice at 56% (w/w) and 60° C., for 48 h gives 63% reduction of phytate.

Incubating the brown rice at 56% w/w in water has not the best impact on the reduction of the phytic acid: the phytic acid content after 48 soaking at 60° C. was reduced with 53%. Using the brown rice at 38% (w/w) in steep water, gives a reduction of 66% after 48 h incubation.

Using a buffer system to steep the brown rice at 56% (w/w) and 60° C., for 48 h gives 63% reduction of phytate.

Example 6—Open System

Same set-up as in example 2. 250 g grains added to 1 l water (=20% d.s grains). Water was added during the steeping in order to have no drying out of the brown rice The pH adjustment of the samples was done as in example 2. The steep temperature and pH are adjusted to obtain the optimum working conditions for the respective phytases.

| Code | Cereal or pulse | T (° C.) | pH | Phytic acid db (g/100 g) | Phytic acid reduction db (%), 24 h incubation | Phytic acid reduction db (%), 48 h incubation |
|---|---|---|---|---|---|---|
| 64 | corn | 55 | 5.5 | 0.891 | 56.6 | 63.7 |
| 65 | wheat | 55 | 5.5 | 0.999 | 52.4 | 59.5 |
| 66 | white beans | 50 | 5.2 | 1.303 | 53.9 | 56.8 |
| 67 | chick pea | 50 | 5 | 1.025 | 43.3 | 47.5 |
| 68 | oats | 50 | 5 | 1.170 | 25.7 | 45.9 |
| 69 | Oats | 45 | 5 | 1.071 | 40.4 | 60.4 |

Example 7: Gelatinization Profiles of Steeped Brown Rice Flours

The Rapid Visocity Analyzer 4 (RVA-4) from Perten was used.
The Perten method Standard-1 was performed in triplicate at 2.1 g (dry basis) solids in 27.9 g demi-water as described in Han, J.-A. & Lim S.-T. (2009). Effect of pre-soaking on textural, thermal, and digestive properties of cooked brown rice. Cereal Chemistry 86(1) 100-105.
Samples 26, 36, 37 and 38 of example 3 were milled and used in the RVA analysis.
All samples were put at a pH of 6.
The obtained results are described in the following table:

| Sample | Peak viscosity (cps) | Peak time (minutes) | Final viscosity (cps) |
|---|---|---|---|
| 26 (start rice, milled) | 542 | 6.05 | 1227 |
| | 563 | 6.05 | 1287 |
| | 564 | 5.92 | 1278 |
| | 556(±12) | 6.01(±0.08) | 1264(±32) |
| 36 (milled) | 242 | 5.58 | 410 |
| | 251 | 5.65 | 414 |
| | 216 | 5.72 | 372 |
| | 236(±18) | 5.65(±0.07) | 399(±23) |
| 37 (milled) | 378 | 6.78 | 790 |
| | 371 | 6.98 | 797 |
| | 337 | 6.58 | 756 |
| | 362(±22) | 6.78(±0.20) | 781(±22) |
| 38 (milled) | 501 | 6.18 | 1011 |
| | 538 | 6.12 | 1067 |
| | 553 | 6.25 | 1079 |
| | 531(±27) | 6.18(±0.07) | 1052(±36) |

The samples 36, that was steeped at a pH of 4 shows a large decrease in final viscosity. The steeping at pH 5 gives an improvement of the final viscosity. By using a steeping pH of 4.5, only 17% of the final viscosity has been lost, while 91% of the phytate has been degraded.

The invention claimed is:

1. A process for treating kernels of cereals and/or pulses, comprising the following steps:
    a) Steeping of the kernels while germination of the kernels is avoided and the kernels are un-milled and the kernels are, without water immersions, soaked in a volume of water that is from 0.8 to 10 times the weight of the kernels, the steeping is performed at a temperature of from 50 to 70° C. during a period of from 8 to 72 hours and during the steeping pH is from 3.5 to 6.5,
    b) Optionally draining excess of water,
    c) Drying the steeped kernels at a temperature of from 50 to 120° C.;
    wherein the process involves only one steeping step.

2. The process according to claim 1 characterized in that steeping of step a) is at a temperature of from 50 to 60° C. and a pH of 3.5 to 6.5.

3. The process according to claim 1 characterized in that the cereals and/or pulses are selected from the group consisting of rice, wheat, oat, soy, corn, chick pea, barley, lentils, and mixtures of two or more thereof.

4. The process according to claim 1 characterized in that the steeped kernels of step c) are reduced in size for producing flour.

5. The process according to claim 1 characterized in that the steeping step is performed in a closed system and the kernels are soaked in a volume of water that is from 0.8 to 4 times the weight of the kernels.

6. The process according to claim 1 characterized in that the steeping step is performed in an open system with aeration and the kernels are soaked in a volume of water that is from 4 to 10 times the weight of the kernels, optionally followed by replenishing with water to compensate for the evaporated water.

7. The process according to claim 1, wherein the phytate content in the kernels is reduced during steeping.

8. The process according to claim 7, wherein the phytate content of the kernels is reduced by at least 50%.

9. The process according to claim 7, wherein the phytate content of the kernels is reduced by endogenous phytase from the kernels.

* * * * *